United States Patent [19]

Dinh et al.

[11] Patent Number: 5,670,688

[45] Date of Patent: Sep. 23, 1997

[54] PROCESS FOR THE INDUSTRIAL MANUFACTURE OF A CYCLOALKYLSILANE OR POLYORGANOSILOXANE

[75] Inventors: Paul Charles Dinh; Binh Thanh Nguyen, both of Midland, Mich.

[73] Assignee: Dow Corning Corporation, Midland, Mich.

[21] Appl. No.: 770,101

[22] Filed: Dec. 19, 1996

[51] Int. Cl.⁶ ..................................................... C07F 7/08
[52] U.S. Cl. .................. 556/453; 556/456; 556/462; 556/466
[58] Field of Search ..................... 556/453, 456, 556/466, 462

[56] References Cited

U.S. PATENT DOCUMENTS

| 2,502,348 | 3/1950 | Scriabine et al. | 252/470 |
| 3,821,305 | 6/1974 | Bartalini et al. | 260/583 |
| 4,777,278 | 10/1988 | Band et al. | 556/480 |
| 4,956,484 | 9/1990 | Gementi et al. | 556/410 |
| 4,977,291 | 12/1990 | Gementi et al. | 556/466 |

FOREIGN PATENT DOCUMENTS 6-271588   3/1994   Japan .

*Primary Examiner*—Paul F. Shaver
*Attorney, Agent, or Firm*—Melvin D. Fletcher

[57] ABSTRACT

This invention relates to a process for the manufacture of a silane or polyorganosiloxane containing a cycloalkyl substituent by hydrogenation of a silane or polyorganosiloxane containing at least one aromatic hydrocarbon substituent in the presence of a Raney nickel catalyst without a solvent.

13 Claims, No Drawings

PROCESS FOR THE INDUSTRIAL MANUFACTURE OF A CYCLOALKYLSILANE OR POLYORGANOSILOXANE

BACKGROUND OF THE INVENTION

This invention relates to a process for the industrial manufacture of a silane or polyorganosiloxane containing a cycloalkyl substituent by hydrogenation of a silane or polyorganosiloxane containing at least one aromatic hydrocarbon substituent in the presence of a Raney nickel catalyst without a solvent.

Gementi et al., described in U.S. Pat. No. 4,956,484 a process for producing cyclohexylmethyldimethoxysilane by catalytic hydrogenation of phenylmethyldimethoxysilane. The hydrogenation was carried out using a Raney nickel catalyst modified with chromium in the presence of n-hexane as a solvent. Unlike the present invention, the '484 patent uses a solvent, thus requiring an additional processing step to remove the solvent from the cyclohexylmethyldimethoxysilane.

Cyclohexylmethyldimethoxysilane can be prepared by the reaction of cyclohexylmagnesium chloride with methyltrimethoxysilane as described in U.S. Pat. No. 4,777,278. Reportedly a 70% to 80% yield was obtained, however often the end product requires additional processing to remove the magnesium chloride salt by-product.

Japanese Patent Application No. 6-271588 disclosed that methylphenyl silicone can be hydrogenated in the presence of a catalyst and solvent as needed to form cyclohexylmethyl silicone.

There remains a need for a process that increases product yield, and decreases manufacturing cost, contaminates and by-product formation due to silane hydrolysis. Furthermore, since Raney nickel is highly pyrophoric and flammable, there is a need for a manufacturing process that ensures safe handling of the catalyst. Finally, there is a need for a process that allows large scale manufacturing of a silane or polyorganosiloxane with at least one cycloalkyl hydrocarbon while eliminating a costly solvent removal step.

SUMMARY OF INVENTION

This invention relates to a process for the industrial manufacture of a silane or polyorganosiloxane containing a cycloalkyl substituent. The process comprises adding a flowable mixture of Raney nickel catalyst and carrier fluid into a reactor. The carrier fluid is then removed from the Raney nickel catalyst under an inert atmosphere. After removing the carrier fluid, hydrogen and a silane or a polyorganosiloxane containing at least one aromatic hydrocarbon substituent are added to the reactor containing the Raney nickel catalyst. The Raney nickel catalyst, the silane or polyorganosiloxane and hydrogen are heated at a temperature sufficient to form a silane or polyorganosiloxane containing a cycloalkyl substituent. The reaction is conducted in the absence of a solvent and eliminates additional cost associated with separating the solvent from the product and results in a higher volume efficiency in the use of the production equipment.

DETAILED DESCRIPTION OF THE INVENTION

Any of the Raney nickel catalysts known for use in hydrogenation reactions of aromatic compounds can be used in this process, but preferable the Raney nickel catalyst is activated with chromium. Most preferably, the chromium content is 0.1 to 5% by weight of nickel. Raney nickel chromium catalysts of this type are known and sold commercially as Raney 2400™ chromium promoted nickel, and Raney 4200™ and are produced by the W. R. Grace Company, U.S.A. These conventional Raney nickel catalysts are further described in U.S. Pat. Nos. 3,821,305 and 2,502,348.

The amount of Raney nickel catalyst used is not critical and may range from 0.01 to 75.0 weight percent of the siloxane or silane and preferably between 0.1 to 50.0 weight percent. However, the handling of Raney nickel is extremely important since it is highly pyrophoric and flammable when exposed to air. Additionally when exposed to air, Raney nickel absorbs oxygen and forms peroxides which can inhibit the reaction. To avoid these hazards, the Raney nickel catalyst is supplied in a flowable mixture of Raney nickel in a carder fluid. The Raney nickel is emerged in the carrier fluid and the carrier fluid provides an inert atmosphere that prevents the Raney nickel catalyst from coming into contact with air, thus avoiding the hazards mentioned. The carder fluid also must be inert and not react with the Raney nickel catalyst.

The carrier fluid is selected from the group consisting of water, mineral oil or any other suitable liquids. Suitable carrier fluids are inert with the Raney nickel and do not aid or hinder, but sole purpose is only to aid handling the Raney nickel catalyst. A suitable carrier fluid is inert and has no effect on the reaction if it is not completely removed from the catalyst, unlike an unsuitable fluid that could react with the silane or product to form by-products.

Silanes which may be hydrogenated contain at least one aromatic hydrocarbon substituent and have the formula of $RR^1_xSi(OR^2)_{3-x}$ wherein x=0, 1 or 2. R is an aryl substituent, such as phenyl and naphthyl. R can also be arylalkyl such as benzyl and 2-phenylethyl. $R^1$ and $R^2$ are independently selected from $C_1$ to $C_6$ alkyl substituent such as methyl, ethyl, propyl, isopropyl, n-butyl, isobutyl, secobutyl, tert-butyl and halogenated alkyls such as $F_3R^1$ and $ClR^1$ and $Br_2R^1$. Silanes of formula $RR^1_xSi(OR^2)_{3-x}$ include benzyldimethylmethoxysilane and phenylalkylalkoxysilanes such as, phenylmethyldimethoxysilane methoxysilane and phenyltrialkoxysilanes such as phenyltriethoxysilane and phenyltrimethoxysilane.

Polyorganosiloxanes which may be hydrogenated are selected from the group consisting of cyclic siloxanes having the formula $(RR^1SiO)_x$ wherein x=3–6 and R is a aryl substituent such as phenyl or naphthyl or arylalkyl substituents such as benzyl or 2-phenylethyl. Also included are linear siloxanes having the formula $R^1_aR_bSiO(RR^1SiO)_ySiR^1_aR_b$, wherein a+b=3, a=0, 1, 2, or 3, b=0, 1, 2, or 3 and y=0 to 500 $R^1$ is defined as above. Suitable linear siloxanes include $(CH_3)_3Si(CH_3PhSiO)_ySi(CH_3)_3$, $(CH_3)_3SiO(CH_3BzSiO)_ySi(CH_3)_3$, and $(CH_3)_2PhSiO(CH_3PhSiO)_ySi(CH_3)_2Ph$, where Ph denotes phenyl and Bz denotes benzyl.

The hydrogenation is carried out at a hydrogen pressure from atmospheric to 35 MPa and a temperature from 20° C. to 300° C. and most preferably from a pressure from 0.5 MPa to 10 MPa and time from 0.5 to 24 hours. The product formed is a silane or polyorganosiloxane containing a cycloalkyl substituent.

In the process steps for carrying out the reaction, the flowable mixture of Raney nickel catalyst and carrier fluid are added to a reactor. The mixture is typically pumped into the reactor, but may be added to the reactor by any other conventional means. Prior to introducing the silane or siloxane, the carrier fluid must be removed. This is a critical process step because any trace of water or other fluid contamination will cause silane hydrolysis resulting in increased by-product formation, low yield, high waste, and overall increased manufacturing cost.

The carrier fluid is removed from the Raney nickel catalyst by filtration, evaporation or any suitable method. An inert atmosphere, such as nitrogen, argon or helium, is used when removing the carrier fluid to prevent the Raney nickel from coming into contact with air and spontaneously igniting. When water is used as the carrier fluid, the Raney nickel is washed with methanol to ensure all water is removed before use. In addition to methanol, toluene, or other solvents compatible with silanes may be used to wash the Raney nickel. Here solvents are only used to wash the Raney nickel and not to speed up the reaction. It is important that the solvents are compatible with the silanes in the event they are not completely removed from the catalyst. A non-compatible solvent could react with the reactant or product to form unwanted by-products.

After removing the carrier fluid and washing the Raney nickel, hydrogen and the silane or polyorganosiloxane are added into the reactor containing the catalyst. The reactants are heated at a temperature from 20° C. and 300° C., at pressure from 0.5 MPa to 10 MPa for a time from 0.5 to 24 hours. The reactor is agitated for 0.5 to 24 hours and the product formed is a silane or polyorganosiloxane containing a cycloalkyl substituent.

The process can be carried out in a batch system, semi-batch system or continuous system. In each system, the Raney nickel catalyst is loaded into the reactor and the carrier fluid removed as described. The Raney nickel catalyst is maintained in the reactor throughout the process by a mechanical means such as a screen basket, or packed bed, suspension bed or fixed bed may be used. In the batch system, the silane or polyorganosiloxane is loaded into the reactor. The reactor is then pressurized with hydrogen reactant gas to 0.5 MPa to 10 MPa. The reactor is heated to the desired temperature and agitated. At completion of the reaction, the product is withdrawn from the reactor. The catalyst may be reused for the next batch.

In the semibatch system, the reactor is loaded with the silane or polyorganosiloxane. The reactor is heated to the temperature as described and hydrogen reactant gas is intermittently fed into the reactor at pressure from 0.5 MPa to 10 MPa as the reactor is agitated. The product is intermittently withdrawn from the reactor.

In the continuous system, the silane or polyorganosiloxane and hydrogen reactant gas are continuously fed into the reactor at a pressure from 0.5 MPa to 10 MPa and temperature from 20° C. and 400° C. The reactor is agitated and the product is continuously withdrawn from the reactor.

The following Examples illustrate certain embodiments of the present invention.

EXAMPLE 1
(Comparison)

Raney Nickel 2400™ (21.5 g) activated chromium catalyst in water solution purchased from W. R. Grace Company, U.S.A., was filtered and washed with absolute methanol to remove all water before use. The Raney nickel catalyst with methanol as the carrier fluid and 100 g of n-hexane were loaded into a Parr™ reactor. Phenylmethyldimethoxysilane (50 g, 0.27 mole), was loaded into the reactor and the reactor sealed. The reactor was pressurized with hydrogen gas to 1.38 MPa and vented 5 times. The reactor was agitated and heated to a temperature of 170°–175° C. After the temperature stabilized, the reactor was charged with hydrogen gas to 5.17 MPa and remained constant over 5 hours at a temperature between 170°–175° C. The reactor was cooled to 20° C. and the excess pressure vented. The reactants were analyzed using gas chromatographic and mass spectrometric analysis which indicated no trace of the product cyclohexylmethyldimethoxysilane. The phenylmethyldimethoxysilane remained unreacted.

EXAMPLE 2

Raney Nickel 2400™ (23.7 g) activated chromium catalyst in water solution purchased from W. R. Grace Company, U.S.A., was loaded into a Parr™ reactor. The water solution was drained from the Raney nickel under a nitrogen blanket, and the Raney nickel was then rinsed with absolute methanol to remove all water before use. The rinsing was repeated 3 times under a nitrogen blanket. The methanol was then drained from the catalyst and approximately 50% of the methanol remained with the catalyst. Phenylmethyldimethoxysilane (50 g, 0.27 mole), was loaded into the reactor and the reactor sealed. The reactor was pressurized with hydrogen gas to 1.40 MPa and vented 5 times. The reactor was agitated and heated to a temperature between 118°–120° C., the reactor was again charged with hydrogen gas until the pressure in the reactor reached 4.83 MPa. After 7 hours, the reactor was cooled to room temperature and the excess hydrogen gas vented. The product was analyzed using gas chromatographic and mass spectrometric analysis which indicated the yield of cyclohexylmethyldimethoxysilane o was 95 area % with 5 area % unreacted starting material.

We claim:

1. A process for the industrial manufacture of a silane or polyorganosiloxane containing a cycloalkyl substituent, the process comprising
   (a) adding a flowable mixture of Raney nickel catalyst and carrier fluid to a reactor,
   (b) removing the carrier fluid from the Raney nickel catalyst under an inert atmosphere,
   (c) after removing the carrier fluid, adding hydrogen and a reactant consisting of a silane or a polyorganosiloxane having at least one aromatic hydrocarbon substituent into the reactor containing the Raney nickel catalyst,
   (d) heating the catalyst and the silane or polyorganosiloxane and hydrogen at a temperature sufficient to form a silane or polyorganosiloxane containing a cycloalkyl substituent.

2. The process of claim 1 wherein the reactant is a silane having the formula of $RR^1{}_xSi(OR^2)_{3-x}$ wherein x=0, 1 or 2, and R is phenyl, naphthyl, benzyl or 2-phenylethyl and $R^1$ and $R^2$ are independently selected from $C_1$ to $C_6$ alkyl substituents.

3. The process of claim 1 wherein the reactant is a polyorganosiloxane selected from the group consisting of cyclic siloxanes having the formula $(RR^1SiO)_x$ wherein x=3–6 and R is phenyl, naphthyl, benzyl or 2-phenylethyl and $R^1$ is independently selected from $C_1$ to $C_6$ alkyl substituents, and linear siloxanes having the formula $R^1{}_aR_bSiO(RR^1SiO)_ySiR^1{}_aR_b$ wherein a+b=3, a=0, 1, 2, or 3, b=0, 1, 2, or 3 and y=0 to 500.

4. The process of claim 2 wherein the silane is phenylmethyldimethoxysilane.

5. The process of claim 1 wherein the Raney nickel catalyst is modified with chromium.

6. The process of claim 1 wherein the carrier fluid is selected from the group consisting of water and mineral oil.

7. The process of claim 1 wherein step (d) is carried out at a pressure from atmospheric to 35 MPa.

8. The process of claim 1 wherein step (d) is carried out at a pressure from 0.5 to 10 MPa.

9. The process of claim 1 wherein step (d) is carried out at a temperature from room temperature to 300° C.

10. The process of claim 1 wherein the catalyst, reactant and hydrogen are heated for 0.5 to 24 hours.

11. The process of claim 1 wherein the carrier fluid is removed by evaporation from the Raney nickel catalyst.

12. The process of claim 1 wherein the carrier fluid is removed by filtration from the Raney nickel catalyst.

13. A process for the industrial manufacture of a silane or polyorganosiloxane containing a cycloalkyl substituent, the process comprising charging a reactor with a flowable mixture of Raney nickel catalyst and carrier fluid, removing the carrier fluid under an inert atmosphere from the Raney nickel catalyst after the reactor is charged, continuously feeding a silane or polyorganosiloxane containing at least one aromatic hydrocarbon substituent into the reactor, continuously feeding hydrogen into the reactor, heating the reactor to a temperature 20° to 300° and forming and continuously removing from the reactor a silane or polyorganosiloxane containing a cycloalkyl substituent.

* * * * *